United States Patent
Randolph et al.

(10) Patent No.: US 9,114,237 B2
(45) Date of Patent: Aug. 25, 2015

(54) SYSTEMS AND METHODS FOR DELIVERING FLUID TO A WOUND THERAPY DRESSING

(71) Applicant: KCI Licensing, Inc., San Antonio, TX (US)

(72) Inventors: Larry Tab Randolph, San Antonio, TX (US); Richard Marvin Kazala, Jr., San Antonio, TX (US); Kevin W. Bendele, La Vernia, TX (US)

(73) Assignee: KCI Licensing, Inc., San Antonio, TX (US)

( * ) Notice: Subject to any disclaimer, the term of this patent is extended or adjusted under 35 U.S.C. 154(b) by 62 days.

(21) Appl. No.: 13/734,790

(22) Filed: Jan. 4, 2013

(65) Prior Publication Data

US 2013/0211348 A1    Aug. 15, 2013

Related U.S. Application Data

(60) Provisional application No. 61/585,055, filed on Jan. 10, 2012.

(51) Int. Cl.
*A61M 35/00* (2006.01)
*A61M 1/00* (2006.01)

(52) U.S. Cl.
CPC ............. *A61M 35/00* (2013.01); *A61M 1/0058* (2013.01); *A61M 1/0084* (2013.01); *A61M 1/0088* (2013.01); *A61M 1/0031* (2013.01); *A61M 2202/0007* (2013.01); *A61M 2210/04* (2013.01)

(58) Field of Classification Search
CPC . A61M 1/0058; A61M 35/00; A61M 1/0088; A61M 1/0084; A61M 1/00; A61M 1/0031; A61M 2001/00; A61M 2001/0023; A61M 2001/0058; A61M 2001/0072; A61M 2202/0007; A61M 2210/04
USPC ................................ 604/290, 304, 313, 305
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Leslie Deak
*Assistant Examiner* — Kai Weng

(57) ABSTRACT

Provided are systems and methods for delivery of fluid to a wound therapy dressing. In exemplary embodiments, a pressure source provides negative pressure to a wound dressing and positive pressure to an actuator that expels fluid from a fluid reservoir.

16 Claims, 3 Drawing Sheets

(56) References Cited

U.S. PATENT DOCUMENTS

| | | | |
|---|---|---|---|
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,180,074 A * | 12/1979 | Murry et al. | 604/31 |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,452,572 A * | 6/1984 | Evrard | 417/395 |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,576,011 A * | 3/1986 | Glamm et al. | 62/115 |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,810,202 A * | 9/1998 | Hoback et al. | 222/95 |
| 6,071,267 A | 6/2000 | Zamierowski | |
| 6,083,195 A * | 7/2000 | Perkins et al. | 604/30 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,398,767 B1* | 6/2002 | Fleischmann | 604/313 |
| 6,413,238 B1* | 7/2002 | Maget | 604/132 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,316,672 B1* | 1/2008 | Hunt et al. | 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0016152 A1* | 1/2007 | Karpowicz et al. | 604/326 |
| 2007/0293830 A1 | 12/2007 | Martin | |
| 2008/0125697 A1* | 5/2008 | Gao | 604/35 |
| 2008/0214994 A1 | 9/2008 | Guignard | |
| 2009/0099545 A1 | 4/2009 | Nilsson et al. | |
| 2011/0184357 A1* | 7/2011 | Robinson et al. | 604/290 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 89/00868 A1 | 2/1989 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 9930758 A1 | 6/1999 |
| WO | 2010/146149 A1 | 12/2010 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding International Application No. PCT/US2013/020360 mailed Apr. 12, 2013.

* cited by examiner

SYSTEMS AND METHODS FOR DELIVERING FLUID TO A WOUND THERAPY DRESSING

CROSS-REFERENCE TO RELATED APPLICATION

This application claims priority to U.S. Provisional Patent Application No. 61/585,055 filed Jan. 10, 2012, entitled SYSTEMS AND METHODS FOR DELIVERING FLUID TO A WOUND THERAPY DRESSING, the disclosure of which is hereby incorporated by reference in its entirety.

BACKGROUND

1. Field

The subject matter of this specification relates generally to healing of wounds and wound-treatment therapies. More particularly, but not by way of limitation, the subject matter relates to systems and methods for improving fluid-instillation and negative pressure wound therapy (NPWT) apparatuses and methods.

2. Discussion

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment.

Typical instillation therapy instills fluid into a wound under a low positive pressure. For maximum therapeutic effect, the instilled fluid should reach all exposed tissue surfaces. The practice of fully filling a wound with instillation fluid, combined with the application of porous wound fillers and negative pressure to help distribute fluid, can provide effective instillation therapy. Such techniques can have numerous disadvantages. For example, filling a wound with fluid is wasteful, particularly where expensive fluids (e.g. antibiotics) are used as the bulk of the fluid enters the dressing (e.g., a foam) to enable the surface of the wound to be coated with instillation fluid.

Even where the instilled fluid is inexpensive, large volumes of fluid may be involved, requiring frequent canister changes that may lead to user dissatisfaction. Although low positive pressures are typically used to fill the wound cavity, the hydraulic (essentially incompressible) nature of the fluid means that over filling can quickly cause drape leakage. Tortuous contours within a wound cavity may be difficult to reach with both foam dressings and liquid-fill techniques as gas pockets may be created. Applying a low vacuum during liquid instillation (to help maintain a seal and reduce leaking, to minimize patient discomfort, and to aid fluid distribution) can be problematic as instilled fluid may be removed before it is fully distributed through the dressing.

The referenced shortcomings are not intended to be exhaustive, but rather are among many that tend to impair the effectiveness of previously known techniques in fluid delivery to wound dressings; however, those mentioned here are sufficient to demonstrate that the methodologies appearing in the art have not been satisfactory and that a significant need exists for the techniques described and claimed in this disclosure. For at least the reasons described above, improved wound treatment systems and methods are therefore desired.

SUMMARY

From the foregoing discussion, it should be apparent that a need exists for a system and method for improved delivery of fluid to a wound therapy dressing. The method in the disclosed embodiments substantially includes the steps necessary to carry out the operation of the described system.

In one embodiment, provided is a system for delivering fluid to a negative pressure wound therapy dressing, where the system includes: an actuator configured to engage a fluid reservoir; and a pressure source configured to provide positive pressure to the actuator and negative pressure to a wound dressing. The actuator can be, for example, configured as a compression sleeve and/or a bladder. Some embodiments may additionally include: a fluid reservoir; a wound dressing; and a fluid control device in fluid communication with the fluid reservoir and the wound dressing.

In specific embodiments, the fluid control device can be a control valve, such as, for example, a solenoid-actuated pinch valve and/or an orifice. Certain embodiments may also include a control system configured to control the fluid control device.

In specific embodiments, the pressure source may include a vacuum diaphragm pump. Specific embodiments may also include a valve in fluid communication with the actuator and the pressure source, where the valve can be configured to vent to atmosphere. The pressure source can be, for example, configured to provide a pressure of between approximately 0.1 psig and approximately 1.0 psig.

In another embodiment, provided is a system for delivering fluid to a negative pressure wound therapy dressing, where the system includes: a pump comprising a vacuum port and a positive pressure port; an expandable member in fluid communication with the positive pressure port, wherein the expandable member is configured to engage a fluid reservoir and expel fluid from the fluid reservoir; and a valve in fluid communication with the positive pressure port and the expandable member, wherein the valve is configured to vent pressure to atmosphere.

Specific embodiments may additionally include a wound dressing in fluid communication with the vacuum port. Further, specific embodiments may additionally include a control system configured to control a fluid flow from the fluid reservoir. For example, the control system can be configured to control a control valve. The control valve can be, for example, a solenoid-actuated pinch valve. In specific embodiments, the positive pressure port can be configured to provide a pressure of between approximately 0.1 psig and approximately 1.0 psig to the expandable member.

In yet another embodiment, provided is a method of delivering fluid to a negative pressure wound therapy dressing, where the method includes: operating a pressure source to exert a positive pressure on a fluid reservoir and a negative pressure on a wound dressing of a negative pressure wound therapy system; monitoring the positive pressure and opening a valve to allow fluid to flow from the fluid reservoir to the wound dressing; closing the valve to restrict fluid flow from the fluid reservoir to the wound dressing; and maintaining negative pressure from the pressure source to the wound dressing.

In specific embodiments, the pressure source may be a diaphragm vacuum pump. In particular embodiments, the positive pressure may be between approximately 0.1 psig and approximately 1.0 psig.

In yet another embodiment, provided is a system for delivering fluid to a wound therapy dressing. The system includes an actuator, a pressure source, and a fluid control device. The actuator is configured to engage a fluid reservoir. Further, the actuator is adapted to expel the fluid from the fluid reservoir. The fluid reservoir is adapted to be in fluid communication with the wound therapy dressing. The pressure source is configured to provide positive pressure to the actuator and negative pressure to the wound therapy dressing. The fluid control device is adapted to be in fluid communication between the fluid reservoir and the wound dressing, wherein fluid communication between the fluid reservoir and the wound dressing is provided through the fluid control device.

In yet another embodiment, provided is a system for delivering fluid to a wound therapy dressing. The system includes a pump, an expandable member, and a valve. The pump comprises a vacuum port and a positive pressure port, the vacuum port being adapted to be in fluid communication with the wound therapy dressing. The expandable member is in fluid communication with the positive pressure port. Further, the expandable member is configured to exert a force on fluid within a fluid reservoir to expel fluid from the fluid reservoir, the fluid reservoir being adapted to be in fluid communication with the wound therapy dressing. The valve is in fluid communication between the positive pressure port and the expandable member, wherein positive pressure from the positive pressure port is provided to the expandable member through the valve, and wherein the valve is configured to vent excess pressure to atmosphere.

In yet another embodiment, provided is a method of delivering fluid to a wound therapy dressing. The method includes the step of operating a pressure source adapted to exert a positive pressure on fluid in a fluid reservoir and a negative pressure on the wound therapy dressing. Further, the method includes monitoring the positive pressure on the fluid. Additionally, the method includes providing a fluid control device adapted to supply the fluid from the fluid reservoir to the wound therapy dressing, the fluid control device comprising a control valve and a metering orifice, the metering orifice being sized to provide a fluid flow rate according to the positive pressure on the fluid. Further, the method includes opening the control valve to provide a predetermined volume of the fluid from the fluid reservoir to the wound therapy dressing, the predetermined volume of the fluid corresponding to the fluid flow rate from the fluid reservoir for an elapsed time period. Even further, the method may include the steps of closing the control valve to restrict the fluid flow from the fluid reservoir to the wound therapy dressing after the elapsed time period, and maintaining negative pressure from the pressure source to the wound dressing.

Other features and associated advantages will become apparent with reference to the following detailed description of specific embodiments in connection with the accompanying drawings.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "negative pressure" refers to an absolute pressure that is lower than the absolute atmospheric pressure at the location of use of the device. A stated level of negative pressure in a region is therefore a relative measure between the absolute atmospheric pressure and the absolute pressure in the region. A statement that the negative pressure is decreasing means the pressure in the region is moving towards atmospheric pressure (i.e. the absolute pressure is increasing). Where numeric values are used a negative sign is placed in front of the numeric pressure value to indicate the value is a negative pressure relative to atmospheric pressure.

BRIEF DESCRIPTION OF THE DRAWINGS

The following drawings form part of this specification and are included to further demonstrate certain aspects of exemplary embodiments of the subject matter described herein.

DETAILED DESCRIPTION OF EXEMPLARY EMBODIMENTS

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
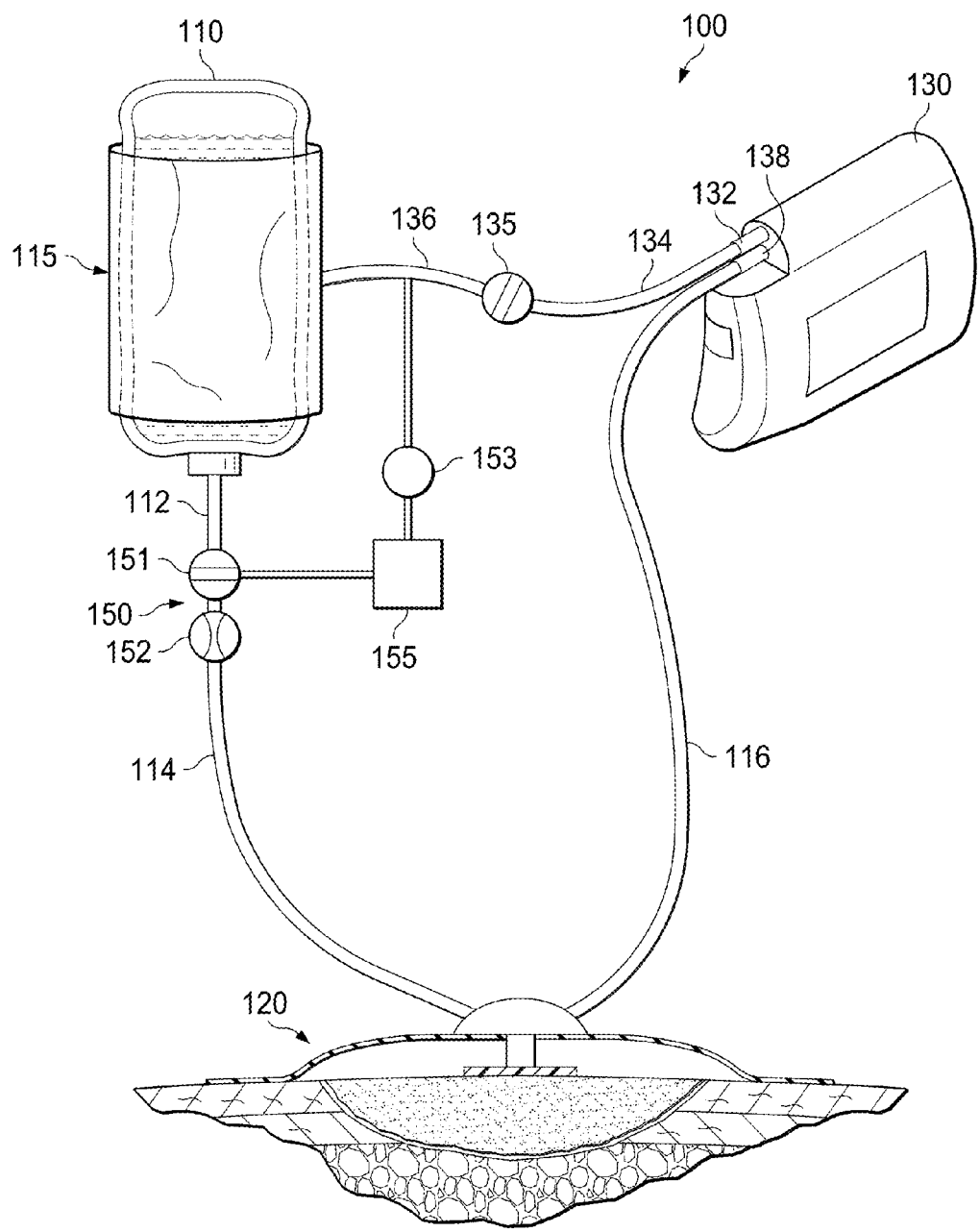
FIG. 1 is a schematic diagram illustrating one embodiment of a system for delivering fluid to a wound therapy dressing.

FIG. 1 illustrates one exemplary embodiment of a system 100 for delivering fluid to a negative pressure wound therapy dressing. In the exemplary embodiment shown, system 100 includes a reservoir 110, a wound dressing 120, and a pressure source 130. In exemplary embodiments, pressure source 130 may be a vacuum pump, including, for example, a diaphragm vacuum pump. In exemplary embodiments, reservoir 110 may be configured as a polyethylene bag similar to those used for intravenous fluid delivery.

In the embodiment of FIG. 1, pressure source 130 provides a negative pressure to reservoir 110 and wound dressing 120, and a positive pressure to an actuator 115 configured to force fluid from reservoir 110. Reservoir 110 may contain saline, antibiotic fluid, or any other fluid suitable for use in instillation therapy. As shown in FIG. 1, actuator 115 is an expandable member, such as a compression sleeve, that is configured to compress reservoir 110 and expel fluid from reservoir 110. For example, FIG. 1 depicts actuator 115 as a compression sleeve positioned circumferentially about reservoir 110. The compression sleeve may be adapted to expand at least in an inward direction toward reservoir 110 to engage and compress reservoir 110, i.e., the internal circumference of the compression sleeve may decrease as the compression sleeve expands.

Continuing with FIG. 1, system 100 additionally includes a fluid control device 150 in fluid communication with reservoir 110 and wound dressing 120. As discussed in greater detail below, fluid control device 150 may comprise one or more valves or orifices configured to control the flow of fluid from reservoir 110 to wound dressing 120.

During operation of system 100, pressure source 130 provides a negative pressure from a vacuum port 138 that is in fluid communication with wound dressing 120 via conduit 116 and with reservoir 110 via conduit 114 and 112. Pressure source 130 is also configured to provide a positive pressure from a pressure port 132 to actuator 115 via conduits 134 and 136 during operation. A valve 135 in fluid communication between pressure port 132 and actuator 115 (e.g. via conduits 134 and 136) can be used to vent positive pressure to atmosphere.

Prior to operation, system 100 is prepared so that actuator 115 is engaged with reservoir 110, containing fluid to be delivered to wound dressing 120. Reservoir 110 is in fluid communication with fluid control device 150 via conduit 112 and with wound dressing 120 via conduit 114. Wound dressing 120 is in turn in fluid communication with vacuum port 138 via conduit 116. Furthermore, pressure port 132 is in fluid communication with actuator 115 via conduits 134 and 136, and valve 135.

Pressure source 130 is operated so that positive pressure is delivered to actuator 115. In certain exemplary embodiments, the pressure provided to actuator 115 is less than 2.0 psig, and in specific embodiments, the pressure level is less than 1.0 psig. In even more specific embodiments, the pressure level is less than 0.9, 0.8, 0.7, 0.6, 0.5, 0.4, 0.3, 0.2 or 0.1 psig.

The pressure level delivered to actuator 115 can be controlled by valve 135. In certain embodiments, valve 135 may be a three-way valve configured to vent excess pressure to atmosphere. Actuator 115 can then exert a force on reservoir 110 so that fluid can be expelled from reservoir 110 via conduit 112.

Fluid control device 150 can be operated to control the amount (e.g., the total volume, the flow rate, or another fluid flow parameter that is desired to be controlled) of fluid expelled from reservoir 110. As shown in FIG. 1, fluid control device 150 includes a control valve 151 and a metering flow orifice 152. Valve 151 may be configured, for example, as a solenoid valve or pinch valve that can be used to stop the flow of fluid from reservoir 110. In certain exemplary embodiments, when valve 151 is closed to stop fluid flow, valve 135 can be positioned to vent the positive pressure developed by pressure source 130 to atmosphere.

It is understood that in other embodiments, fluid control device 150 may comprise a different combination of components, including for example, a control valve without an orifice or an orifice without a control valve. In certain embodiments, fluid control device 150 may be controlled via an appropriate control system 155 (e.g., a system comprising software, pressure sensors or other appropriate components). For example, control system 155 may receive an input from a pressure sensor 153 configured to detect a pressure exerted on actuator 115. As shown in FIG. 1, pressure sensor 153 detects pressure in conduit 136, wherein conduit 136 is in fluid communication with actuator 115. Control system 155 may also be configured to provide an output to valve 151 to control the flow of fluid from reservoir 110, based on, for example, the pressure exerted on actuator 115 and the force, or pressure, exerted by the actuator 115 on reservoir 110 and the fluid therein.

Fluid control device 150 can be operated so that a known, or predetermined, volume and/or flow rate of fluid is expelled from reservoir 110 based on the known pressure level exerted on reservoir 110 and the valve position and/or orifice size of control device 150. In particular embodiments, the rate of fluid flow from reservoir 110 may be controlled at 100 ml/minute. In other embodiments, the flow rate may be controlled at 90, 80, 70, 60, 50, 40, 30, or 10 ml/min.

By utilizing a positive pressure to expel fluid from reservoir 110 and fluid control device 150 to control the fluid flow from reservoir 110, a user can precisely monitor and administer a desired amount of fluid to wound dressing 120. For example, metering flow orifice 152 can be sized to provide a particular flow rate at a known pressure provided to reservoir 110. The flow rate can be maintained at a substantially constant level because actuator 115 can expand as the volume in reservoir 110 is reduced. With a known flow rate, valve 151 can be operated for a specific length of time to provide a desired fluid volume to wound dressing 120, i.e., the predetermined or desired volume of fluid from reservoir 110 may correspond to the fluid flow rate from reservoir 110 for an elapsed time period. This can reduce the likelihood that excess fluid will be delivered to wound dressing 120 and cause leakage.

Figure 2:
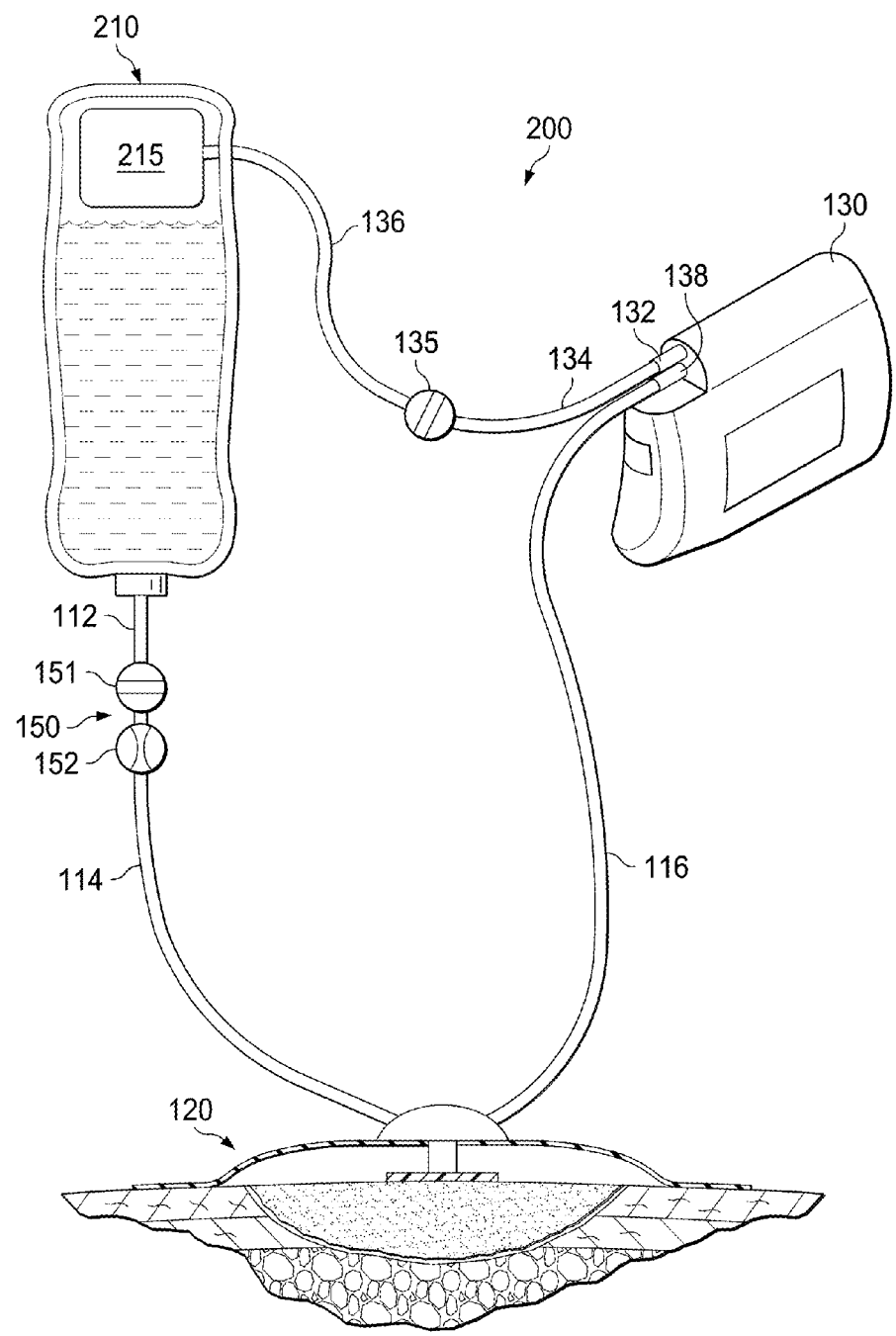
FIG. 2 is a schematic diagram illustrating another embodiment of a system for delivering fluid to a wound therapy dressing.

The embodiment shown in FIG. 1 is merely one exemplary embodiment. Other exemplary embodiments may comprise a different configuration or arrangement of components. For example, referring now to FIG. 2, an exemplary embodiment of a system 200 is shown that is similar to that of FIG. 1, but includes an actuator 215 that is configured as an expandable bladder. The components of system 200 sharing the same element numbering as the components discussed in connection with system 100 are equivalent, and thus, will not be further described herein.

During operation of system 200, actuator 215 expands as the pressure provided from pressure source 130 is increased. In this embodiment, actuator 215 is contained within a reservoir 210, such as a housing. As actuator 215 expands, actuator 215 displaces fluid in reservoir 210 to expel fluid from reservoir 210 in a similar manner as described above in connection with system 100 to provide controlled fluid flow from reservoir 210 to wound dressing 120.

Figure 3:
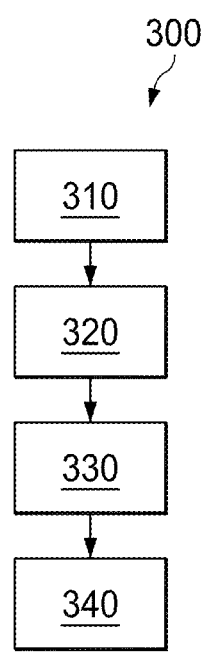
FIG. 3 is schematic flowchart diagram illustrating one embodiment of a method for delivering fluid to a wound therapy dressing.

Referring now to FIG. 3, a flow chart is provided to illustrate an embodiment of a method that may be utilized to operate systems 100 and 200. The flow chart is generally set forth as a logical flow chart diagram. As such, the depicted order and labeled steps are indicative of one non-limiting embodiment of the presented method. Other steps, methods, and the order of execution thereof may be conceived that fall within the scope of this specification.

In the embodiment shown in FIG. 3, a method 300 is disclosed comprising a series of steps that may be executed for the operation of an exemplary system according to this disclosure. Certain embodiments may comprise a tangible computer readable medium comprising computer readable code that, when executed by a computer, causes the computer to perform operations comprising the steps disclosed in FIG. 3.

In this exemplary embodiment, step 310 comprises operating a pressure source to exert a positive pressure on a fluid reservoir and to exert a negative pressure on a wound dressing of a negative wound pressure therapy system. Step 320 comprises monitoring a reservoir or fluid pressure and opening a valve to allow fluid to flow from the fluid reservoir to the wound dressing. Step 330 comprises closing the valve to restrict fluid flow from the fluid reservoir to the wound dressing. Step 340 comprises maintaining negative pressure from the pressure source to the wound dressing. The method may additionally include the steps of providing the previously described fluid control device 150, opening control valve 151 associated with fluid control device 150, and subsequently closing control valve 151 after an elapsed time period sufficient to deliver a predetermined volume of fluid from reservoir 110, 210.

While the apparatus and methods herein have been described in terms of preferred embodiments, it will be apparent to those of skill in the art that variations may be applied without departing from the scope of this specification as defined by the appended claims.

We claim:

1. A system for delivering fluid to a wound therapy dressing, the system comprising:
   an actuator configured to engage a fluid reservoir, the actuator adapted to expel fluid from the fluid reservoir, wherein the fluid reservoir is adapted to be in fluid communication with the wound therapy dressing;
   a pressure source configured to provide positive pressure to the actuator and negative pressure to the wound therapy dressing;
   a fluid control device in fluid communication between the fluid reservoir and the wound therapy dressing;
   a pressure sensor configured to detect a pressure exerted on the actuator;
   a control system configured to control fluid flow based on the pressure exerted on the actuator, wherein the control system is configured to regulate the positive pressure being delivered to the actuator and to communicate with the fluid control device to regulate fluid leaving the fluid reservoir in response to the pressure detected by the pressure sensor; and
   a valve in fluid communication between the actuator and the pressure source, wherein the positive pressure is provided to the actuator through the valve, wherein the valve is configured to vent excess pressure from the pressure source to atmosphere and wherein the valve the valve is in communication with the control system and further configured to regulate the positive pressure delivered to the actuator in response to a signal from the control system.

2. The system of claim 1, wherein the actuator is a compression sleeve positioned circumferentially about the fluid reservoir, the compression sleeve adapted to compress the fluid reservoir and to expel fluid from the fluid reservoir upon application of the positive pressure.

3. The system of claim 1, wherein the actuator is an expandable bladder positioned within the fluid reservoir, the expandable bladder adapted to expand upon application of the positive pressure to displace the fluid in the fluid reservoir and to expel the fluid from the fluid reservoir.

4. The system of claim 1, wherein the fluid control device comprises a control valve and a metering flow orifice, wherein the control valve and the metering flow orifice cooperate to provide a volume of the fluid from the fluid reservoir according to the positive pressure provided to the actuator and a size of the metering flow orifice.

5. The system of claim 4, wherein the control valve is selected from the group consisting of: a solenoid valve and a solenoid-actuated pinch valve.

6. The system of claim 1, wherein the fluid control device comprises a control valve selected from the group consisting of: a solenoid valve and a solenoid-actuated pinch valve.

7. The system of claim 1, wherein the fluid control device comprises a metering flow orifice.

8. The system of claim 1, wherein the control system is operable on the fluid control device to provide a volume of the fluid from the fluid reservoir according to the pressure exerted on the actuator.

9. The system of claim 1, wherein the pressure source comprises a vacuum diaphragm pump, the vacuum diaphragm pump having a vacuum port and a positive pressure port, the vacuum port adapted to provide the negative pressure to the wound therapy dressing and the positive pressure port adapted to provide the positive pressure to the actuator.

10. The system of claim 1, wherein the pressure source is configured to provide a pressure of between approximately 0.1 psig and approximately 1.0 psig.

11. The system of claim 1, wherein the pressure sensor is in fluid communication with the actuator.

12. The system of claim 1, wherein the valve is a three-way valve.

13. The system of claim 4, wherein the control valve is adapted to be in fluid communication between the fluid reservoir and the metering flow orifice, and wherein the control system is configured to control the control valve.

14. The system of claim 1, wherein the pressure sensor is in fluid communication between the valve and the actuator.

15. The system of claim 1, wherein the fluid control device comprises a control valve and a metering flow orifice, wherein the metering flow orifice is sized to provide a fluid flow rate based on the pressure exerted on the actuator and the fluid reservoir.

16. The system of claim 1, wherein the valve is further configured to vent the positive pressure to atmosphere in response to a stop of fluid flow at the fluid control device.

* * * * *